United States Patent [19]

Dichtelmuller et al.

[11] Patent Number: 5,011,695

[45] Date of Patent: Apr. 30, 1991

[54] STERILIZATION OF BLOOD AND ITS DERIVATIVES WITH VITAMINS

[75] Inventors: Herbert Dichtelmuller, Sulzbach/Ts.; Wolfgang Stephan, Dreieich, both of German Democratic Rep.

[73] Assignee: Biotest Pharma GmbH, Dreieich, Fed. Rep. of Germany

[21] Appl. No.: 311,483

[22] Filed: Feb. 16, 1989

[30] Foreign Application Priority Data

Feb. 22, 1988 [DE] Fed. Rep. of Germany ....... 3805459

[51] Int. Cl.$^5$ ..................... A61K 35/14; A61K 35/16; C12N 7/06
[52] U.S. Cl. ..................... 424/529; 424/530; 514/52; 514/276; 514/458; 514/474; 514/725; 435/236; 435/238; 422/28; 422/30
[58] Field of Search ....................... 424/101, 529, 530; 435/236, 238; 422/28, 30; 514/52, 276, 458, 474, 725

[56] References Cited

U.S. PATENT DOCUMENTS

| | | | |
|---|---|---|---|
| 1,556,120 | 10/1925 | Mills | 422/30 |
| 4,179,338 | 12/1979 | Gordon | 435/243 |
| 4,446,134 | 5/1984 | Naito et al. | 424/101 |
| 4,481,189 | 11/1984 | Prince | 424/101 |
| 4,610,814 | 9/1986 | Dede et al. | 424/101 |
| 4,820,805 | 4/1989 | Neurath et al. | 530/410 |
| 4,845,074 | 7/1989 | Rubinstein | 514/2 |

FOREIGN PATENT DOCUMENTS 127605  12/1984  European Pat. Off. ............ 424/101

OTHER PUBLICATIONS

Murata et al., Chem. Abstracts, vol. 102 (1985) 218208v.
Murata et al., Chem. Abstracts, vol. 103 (1985) 51128a.

*Primary Examiner*—Jacqueline Stone
*Attorney, Agent, or Firm*—Sprung Horn Kramer & Woods

[57] ABSTRACT

A method for sterilizing blood, plasma or derivatives thereof by using vitamins or provitamins.

21 Claims, No Drawings

STERILIZATION OF BLOOD AND ITS DERIVATIVES WITH VITAMINS

The invention relates to a method for sterilization of blood, plasma, blood- and plasma derivatives, cell suspensions or similar with a physiologically innocuous sterilant.

Human blood or human plasma or derived products potentially entail the risk of transmitting viral infection. In particular, human pathogenic lipid viruses such as HIV, HNANBV and HBV play a special role. For this reason, preparations derived from human blood or plasma must be virus inactivated.

Clotting preparations such as F VIII or F IX concentrates can be sterilized by means of heat (EP 0 037 078), but require appreciable amounts of stabilizers in order to stand such a treatment. In other methods, the preparation is heated in the lyophilized state, with additional use of organic solvents, pressure or steam in combination.

Chemical agents such as a combination of lipid solvents and detergents or beta-propiolactone in combination with UV irradiation (EP 0 014 333) are also used.

All these methods display various advantages, but also disadvantages which impair the application or the efficacy. The substances in solution added for heat sterilization must be removed again in the clotting factor end product. In heating in the lyophilized state, the poorly standardized residual moisture content determines the effectiveness of the method. In addition, numerous components of the blood cannot be lyophilized. Beta-propiolactone/UV can be used to sterilize F VIII only with loss of yield. Solvents and detergents must be removed again from biological material by elaborate processes.

So far, sterilization of cell suspensions is not possible. For example, heat sterilization methods are not suitable for erythrocyte suspensions, since the cells are destroyed. Chemical methods (detergents, solvents or beta-propiolactone) also bring about complete or partial hemolysis of the cells. Suspensions of white blood cells also cannot be sterilized with this method.

To summarize, unphysiological conditions and substances are used in all the sterilization methods so far described.

The invention is based on the task of providing a virus inactivation procedure which works under physiological conditions and with physiological substances, which is suitable for sterilization of blood/plasma or their derivatives as well as for cell suspensions. A physiologically well-tolerated substance which can remain in the biological material to be sterilized is used as sterilizing agent.

In accordance with the invention, this problem was resolved by use of vitamins or water soluble salts thereof as sterilizing agents. Vitamins are natural physiological substances of which the anti-infectious, health-promoting activity is already known. Moreover, vitamins do not have to be removed from the biological material to be sterilized, since the human body relies on supply of vitamins. Preferred vitamins are vitamin A, B, $B_1$, $B_6$, $B_{12}$, C and E. Preferred salts are the acetates, such as vitamin A- and E-acetate.

Sterilization is carried out in that the biological material to be sterilized is mixed with 0.01 to 1.0 weight % of a vitamin (per volume% sterilisate) and preferably 0.2%, the pH value is adjusted to 5.6 to 8.5 and incubation is carried out with stirring for up to 24 hours at 10° C. to 50° C. Preferentially, the pH value is 7.15 and the temperature is 23° C. to 37° C., and more preferentially 23° C. or 37° C. The preferred sterilization time is three to four hours. If necessary, a dissolution mediator can be added to improve the solubility of the vitamin. A preferred solubilizer is e.g. Tween 80.

The method in accordance with the invention enables virus inactivation in blood, blood cells, blood plasma, blood serum, constituents of blood cells (e.g. interferons, interleukins or hemoglobins, red cell concentrates or concentrates of other cellular blood compounds as granulocytes, platelets, lymphocytes etc.) as well as plasma derivatives (e.g. plasma cryopoor plasma, coagulation factors, cryoprecipitate (e.g. factor VIII, IX, X, XIII etc.), immunoglobulines, the inhibitors $a_1$ antitrypsin, antithrombin III etc.).

The sterilizing agent, i.e. the vitamin, can remain in the biological material to be virus inactivated but it also may easily be removed from the sterilized preparation by means of washing gelfiltration, adsorption or ultrafiltration.

In the examples below, Sendai viruses were used to demonstrate virus inactivation in accordance with the discovery. Sendai viruses have been proved to be very effective in experiments as model viruses for the human pathogenic lipid viruses HBV, HNANBV and HIV. Moreover Herpes virus HSV-I has been used.

EXAMPLE 1

Sterilization of Plasma by Means of Vitamin C 100 ml human plasma were mixed with 0.2% vitamin C after the plasma had been contaminated with Sendai virus. The mixture was incubated for four hours at 23° C. and pH 7.15.

A reference sample which was also contaminated with Sendai virus was incubated under the same conditions but without addition of the vitamin. The samples were frozen immediately after incubation at −80° C. The infectious titers of Sendai virus were determined on incubated eggs. In the reference sample, a titer of $10^{2.7}$ infectious units/ml was found. In the sample with vitamin C, infectious virus was no longer demonstrated, corresponding to an inactivation of $\geq 2.7$ $\log_{10}$.

EXAMPLE 2

Human erythrocytes, washed three times with 0.9% sodium chloride, were spiked with Sendai virus (dilution 1:100). 0.25% vitamin E-acetate was added to one aliquot of the virus spiked erythrocytes and the mixture incubated at 37° C. for 3 hours. The second virus spiked aliquot was incubated without vitamin addition. In all the following examples, the control sample was treated identically. Infectious Sendai virus was titrated in embryonated eggs and antigen determined by haemagglutination assay.

In the vitamin E-acetate treated sample no infectious Sendai virus was detectable, whereas in the untreated sample $5 \times 10^4$ Sendai/ml were found, corresponding to a reduction of virus titer of $>4.7$ $\log_{10}$ (Table I).

TABLE I

Inactivation of Sendai virus in human erythrocyte concentrate by vitamin E

| Virus Treatment | Titer untreated contr. | Titer Vit. E. treated | Inactivation ($\log_{10}$) |
|---|---|---|---|
| Sendai Vit. E. ace- | $5 \times 10^4$ | $<10^0$ | $>4.7$ |

TABLE I-continued

Inactivation of Sendai virus in human
erythrocyte concentrate by vitamin E

| Virus Treatment | Titer untreated contr. | Titer Vit. E. treated | Inactivation ($\log_{10}$) |
|---|---|---|---|
| tate, 0.25% 3 h, 37° C. | | | |

EXAMPLE 3

Human, erythrocytes, washed three times, were spiked with Herpes virus (HSV-I) and treated as described in Example 2, using vitamin E acetate, supplemented with Tween 80 (0.075%/0.01%) for better solubility.

Herpes virus was titrated on cell culture (Rita-cells) by plaque counting. The results are given in Table II. Tween 80 alone shows almost no virus inactivation activity. Even concentrations ten times higher than those used in the combination with vitamin E are ineffective.

TABLE II

Inactivation of Herpes virus (HSV-I) in human
erythrocyte concentrate by vitamin E

| Virus | Treatment | Inactivation ($\log_{10}$) |
|---|---|---|
| Herpes | vitamin E acetate + Tween 80 (0.15% + 0.037%) | 2.7 |
| | vitamin E acetate + Tween 80 0.05% + 0.01% | 2.3 |
| | vitamin E + Tween 80 0.01% + 0.002% | 1.3 |
| | Tween 80 0.15% | 0.3 |

EXAMPLE 4

Human plasma was spiked with Sendai virus (dilution 1:50) and one aliquot of the spiked plasma was incubated in the presence of 0.2% vitamin A acetate at 23° C. for three hours. Virus titration was performed as described in Example 1. Treatment with vitamin A acetate resulted in a titer reduction of Sendai virus of $>2.7 \log_{10}$ (Table III).

EXAMPLE 5

Human plasma was spiked with Sendai virus as described in Example 4 and treated with vitamin A acetate (0.5%) supplemented with Tween 80 (0.15%).

Due to this treatment inactivation of Sendai virus of 2.0 $\log_{10}$ was achieved (Table III).

TABLE III

Inactivation of Sendai virus by vitamin E
acetate in human plasma

| Virus | Treatment | Inactivation ($\log_{10}$) |
|---|---|---|
| Sendai | Vit A. acetate (0.2%) | >2.7 |
| | (Vit. A acetate + Tween 80 0.5% + 0.15%) | 2.0 |

EXAMPLE 6

Human plasma was spiked with Sendai virus and treated with vitamin $B_6$ (0.2%). Incubation was performed at 23° C. for three hours. Titration of Sendai virus was performed as described above. Titer of infectious Sendai virus was reduced by treatment with vitamin $B_6$ by $>2.7 \log_{10}$ (Table IV). Treatment with 0.1% vitamin $B_6$ resulted in an inactivation of 1.0 $\log_{10}$.

EXAMPLE 7

Human plasma was spiked with Sendai virus and treated with vitamin $B_{12}$ (0.2%). The inactivation of Sendai virus achieved by treatment with vitamin $B_{12}$ was $>2.7 \log_{10}$ (Table IV).

TABLE IV

Inactivation of Sendai virus in human plasma
by vitamin B

| Virus | Vitamin | Treatment | Inactivation ($\log_{10}$) |
|---|---|---|---|
| Sendai | $B_6$ | 0.2% 3 hr, 23° C. | >2.7 |
| Sendai | $B_6$ | 0.1% 3 hr, 23° C. | 1.0 |
| Sendai | $B_{12}$ | 0.2% 3 hr, 23° C. | >2.7 |

EXAMPLE 8

Human erythrocytes, washed as described, were spiked with Herpes virus (HSV-I) and treated with vitamin A acetate (0.2%) plus Tween 80 (0.075%). The reduction of infectious HSV-I titer by this treatment was 2.0 $\log_{10}$ (Table V).

EXAMPLE 9

Human erythrocytes were spiked with Herpes virus (HSV-I) and treated with vitamin $B_{12}$. The titer of infectious HSV-I was reduced by treatment with vitamin $B_{12}$ by 1.0 $\log_{10}$ (Table V).

TABLE V

Inactivation of Herpes virus (HSV-I) in human
erythrocytes by vitamin A and $B_{12}$

| Virus | Vitamin | Treatment | Inactivation ($\log_{10}$) |
|---|---|---|---|
| HSV-I | A-ac. (0.2%) + Tween (0.075%) | 3 hr, 37° C. | 2.0 |
| HSV-I | $B_{12}$ (0.2%) | 3 hr, 37° C. | 1.0 |

It will be understood that the specification and examples are illustrative but not limitative of the present invention and that other embodiments within the spirit and scope of the invention will suggest themselves to those skilled in the art.

We claim:

1. A method for sterilizing a lipid-coated-virus-containing member selected from the group consisting of blood, a blood derivative, plasma or a plasma derivative consisting essentially of treating said member with an agent selected from the group consisting of vitamin A, vitamin E, vitamin $B_6$, vitamin $B_{12}$ and vitamin C or a mixture thereof.

2. The method according to claim 1, wherein the vitamin or provitamin is employed in the form of a water-soluble salt.

3. The method according to claim 1, wherein the sterilizing agent is a mixture of different vitamins.

4. The method according to claim 1, wherein the sterilizing agent comprises vitamin A.

5. The method according to claim 1, wherein the sterilizing agent comprises vitamin E.

6. The method according to claim 1, wherein the sterilizing agent comprises vitamin $B_6$, $B_{12}$ or C.

7. The method according to claim 2, wherein the sterilizing agent comprises at least one of vitamin A acetate and vitamin E acetate.

8. The method according to claim 6, wherein the sterilizing agent comprises a member selected from the group consisting of vitamins $B_6$ and $B_{12}$.

9. The method according to claim 1, wherein the treatment is effected in the presence of a substance capable of improving the solubility of the vitamin in aqueous solution.

10. The method according to claim 9, wherein the substance comprises Tween 80.

11. The method according to claim 1, wherein the vitamin is employed in about 0.01 to 1 weight % per volume % sterilizate.

12. The method according to claim 1, wherein the vitamin is employed in about 0.2 to 1 weight % per volume % sterilizate.

13. The method according to claim 1, wherein the treatment is effected at about 10° to at most about 50° C.

14. The method according to claim 1, wherein the treatment is effected at about 23° to 37° C.

15. The method according to claim 1, wherein the treatment is effected at about 23° or 37° C.

16. The method according to claim 1, wherein the treatment is effected over about 1 to 24 hours.

17. The method according to claim 1, wherein the treatment is effected over about 3 to 4 hours.

18. The method according to claim 1, wherein the material sterilized comprises a concentrate of red cells, granulocytes, platelets, lymphocytes or blood serum.

19. The method according to claim 1, wherein the material sterilized comprises plasma, a cryo poor plasma, a coagulation factor, a cryoprecipitate or an immunoglobulin.

20. The method according to claim 1, wherein the material sterilized comprises $\alpha$, antitrypsin or antithrombin III.

21. The method according to claim 1, including the further step of subjecting the mixture of member being sterilized and sterilizing agent to washing, gel filtration, adsorption or ultrafiltration to separate the sterilizing agent from the sterilized material.

* * * * *

UNITED STATES PATENT AND TRADEMARK OFFICE
CERTIFICATE OF CORRECTION

PATENT NO. : 5,011,695

DATED : April 30, 1991

INVENTOR(S) : Dichtelmuller et al.

It is certified that error appears in the above-identified patent and that said Letters Patent is hereby corrected as shown below:

Title Page    [75] Inventors:  3rd line delete " German Democratic Rep. " and substitute -- Fed. Rep. of Germany --

Signed and Sealed this

First Day of June, 1993

Attest:

MICHAEL K. KIRK

Attesting Officer

Acting Commissioner of Patents and Trademarks